United States Patent [19]

Moore

[11] Plant 4,028

[45] Mar. 29, 1977

[54] MINIATURE ROSE PLANT

[76] Inventor: Ralph S. Moore, 2519 E. Noble Ave., Visalia, Calif. 93277

[21] Appl. No.: 651,953

[22] Filed: Jan. 23, 1976

[51] Int. Cl.[2] ..... A01H 5/00

[52] U.S. Cl. ..... Plt./8

[58] Field of Search ..... Plt./8

*Primary Examiner*—Robert E. Bagwill

EXEMPLARY CLAIM

1. A new and distinct variety of miniature rose plant of hardy, dwarf, rounded, much branched, bush type as illustrated and described, characterized by buds and flowers resembling the Easter Morning (U.S. Plant Pat. No. 2,177) miniature rose in general form and size but color is rich clear yellow with better than average lasting quality, the general color effect being deep yellow; and further characterized by a plant which is of vigorous and compact growth, easy to propagate from cuttings, with medium small semi-glossy foliage and an abundance of bloom, with flowers borne singly or several to stem in loose clusters.

1 Drawing Figure

The present invention relates to a new and distinct variety of hardy, dwarf, bush type rose plant of the miniature class; the variety being primarily characterized — as to novelty — by deep yellow buds and flowers which in general color effect are clear rich yellow when grown either outdoors or in greenhouse.

The variety is further characterized by:

An abundance of bloom, with flowers borne singly or several to the stem in loose clusters.
Moderate fragrance.

A plant which is vigorous, of rounded to somewhat spreading shape, and with semi-glossy to glossy, small foliage with pointed leaflets; the flowers and foliage being similar to the variety Easter Morning (miniature — U.S. Plant Pat. No. 2,177) except that buds and flowers are deep yellow. The plant has a normal average height of 12 to 14 inches at maturity but may be easily maintained at lesser height by occasional trimming.

A plant which grows and blooms satisfactorily both in greenhouse and outdoors; is a good plant for growing in pots; and provides excellent garden decoration as well as cut flowers.

The present variety of miniature rose was originated by me at my nursery located at Visalia, Calif., under conditions of careful control and observation, as a cross between Golden Glow, a large flowered climber (U.S. Plant Pat. No. 263, expired), as the seed parent and an unnamed white miniature (seedling — not patented) as the pollen parent.

Subsequent to origination of the variety I successfully asexually reproduced it in my nursery located as aforesaid, by budding as well as by cuttings; the reproductions having run true in all respects.

Referring now specifically to the new and distinct variety of miniature rose plant, the following is a detailed description thereof in outline; all major color plate identification being by reference to the British Colour Council Horticultural Colour Chart, except where common terms of color definition are employed.

Type: hardy; dwarf; bush; seedling; greenhouse; outdoors; cut flowers; garden decoration; potted plant.
Class: Miniature.

Flowers:
- *Continuity.*—Continuous.
- *Fragrance.*—Moderate, sweet.

Flowers borne: Singly and several together (3 to 5) on normal strength medium length stems.

Quantity of bloom: Abundant both outside and in greenhouse.

Bud: Peduncle — medium to long; slender; erect; medium green; some short prickles. Before calyx breaks: size — small. Form medium long; pointed with some foliaceous appendages on surface of the bud; with foliaceous parts extending beyond the tip of the bud equal to one-half or more of its length. Color — medium green, sometimes tinted bronze (outdoors). As calyx breaks, color — yellow. As first petal opens: yellow. Form: medium length, pointed; becoming short urn or bowl shaped. Opening: opens well in all weather.

Bloom:
- *Size when fully open.*—Medium small, averaging 4 cm (about 1½ inches).
- *Petalage.*—Very double — up to 50 or more petals (plus several narrow petaloids) arranged regularly.
- *Form.*—Full, rounded at first, with petals rolled loosely outward, and later at maturity becoming flatter with petals rolled outward and folded to give quilled or pointed effect.

Petals: Thick; satiny both inside and outside. Shape: outside petals nearly round (broad lanceolate with small (short) acute tip); intermediate — broad lanceolate with rounded tip; inside — narrow lanceolate.

Color: Newly opened flower from plant grown in plastic greenhouse (Jan. 16, 1976), Visalia, Calif.
- *Outside petal.*—Outside surface — near Chinese Yellow 606, with tip area shading near Straw Yellow 604; inside surface — near Straw Yellow 604 with darker shading near base.
- *Intermediate petal.*—Outside surface — similar to outside petal; inside surface — similar to outside petal.
- *Inner Petal.*—Outside surface — essentially same as intermediate petal; inside surface — essentially same as intermediate petal.

General color effect — newly opened flower — deep yellow. Three days open — essentially same color.

Behavior — spent petals may hang on for a time. Flower color is very lasting even in warm weather. Flower longevity (June 1975) — bush in garden or pot — 5 to 7 days or longer. Cut flowers at living room temperature — 4 to 7 days.

Reproductive Organs:

*Stamens.*—Few to moderate number.

*Filaments.*—Uneven length, yellow. Anthers: yellow.

*Pollen.*—Some.

*Pistils.*—Several.

*Styles.*—Uneven; medium length; bunched.

*Ovaries.*—All enclosed in calyx.

*Hips.*—Some.

*Sepals.*—Permanent; spear shaped; recurved.

*Seeds.*—Some; some may germinate.

Foliage:

*Leaves.*—Compound of five leaflets (sometime seven); abundant; moderately small; leathery; semi-glossy.

*Leaflets.*—Shape: lanceolate; apex acute; base rounded or rounded acute. Margin serrate. Color: normal green; new growth usually normal green. Rachis: medium strength; upper side slightly hairy, grooved, underside sparsely thorny. Stipules: medium length; narrow; short to medium length points turning out at an angle of 45° or more.

Growth:

*Habit.*—Dwarf; bushy; rounded; much branched.

*Growth.*—Free; vigorous.

*Canes.*—Medium; slender.

*Main Stems.*—Color: dull green. Thorns — moderately thorny; medium length; hooked slightly downward; color — gray brown. Prickles — none. Hairs — none.

*Branches.*—Color: medium green. Thorns: moderately thorny; short; hooked slightly downward; medium length oval base. Prickles — none. Hairs — none.

*New shoots.*—Color: medium green. Thorns — moderately thorny; reddish to light brown; hooked slightly downward; sharp points, base oval.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type as illustrated and described, characterized by buds and flowers resembling the Easter Morning (U.S. Plant Pat. No. 2,177) miniature rose in general form and size but color is rich clear yellow with better than average lasting quality, the general color effect being deep yellow; and further characterized by a plant which is of vigorous and compact growth, easy to propagate from cuttings, with medium small semi-glossy foliage and an abundance of bloom, with flowers borne singly or several to stem in loose clusters.

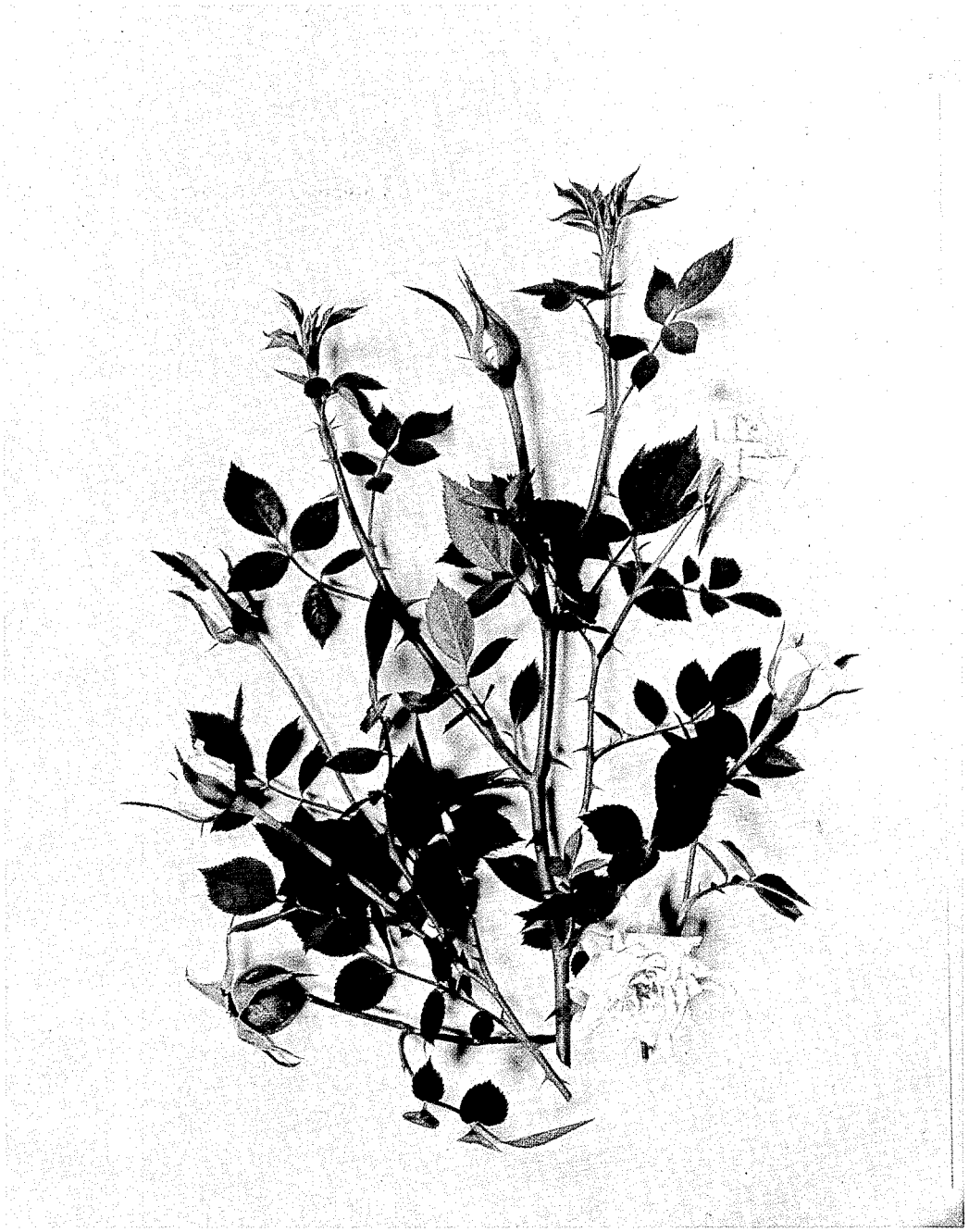

* * * * *